United States Patent [19]

Guskey et al.

[11] Patent Number: 5,492,714
[45] Date of Patent: Feb. 20, 1996

[54] REDUCED CALORIE FATS WHICH COMPRISE REDUCED CALORIE TRIGLYCERIDES CONTAINING MEDIUM AND LONG CHAIN FATTY ACIDS AND WHICH EXHIBIT RAPID CRYSTALLIZATION TO BETA PHASE

[75] Inventors: Gerald J. Guskey, Montgomery; James A. Hellyer, Milford; Bernard W. Kluesener, Harrison; Gordon K. Stipp, Cincinnati, all of Ohio

[73] Assignee: The Procter & Gamble Company, Cincinnati, Ohio

[21] Appl. No.: 336,360

[22] Filed: Nov. 8, 1994

[51] Int. Cl.$^6$ ..................................................... A23D 9/00
[52] U.S. Cl. ............................................. 426/607; 426/804
[58] Field of Search ............................... 426/804, 660, 426/607

[56] References Cited

U.S. PATENT DOCUMENTS

| | | | |
|---|---|---|---|
| 4,832,975 | 5/1989 | Yang | 426/607 |
| 4,859,483 | 8/1989 | Sollich | 426/519 |
| 4,888,196 | 12/1989 | Ehrman et al. | 426/601 |
| 5,023,106 | 6/1991 | Ehrman et al. | 426/660 |
| 5,066,510 | 11/1991 | Ehrman et al. | 426/607 |
| 5,120,563 | 6/1992 | Mohlenkamp, Jr. et al. | 426/601 |
| 5,142,071 | 8/1992 | Kluesener et al. | 554/172 |
| 5,142,072 | 8/1992 | Stipp et al. | 554/172 |
| 5,258,197 | 11/1993 | Wheeler et al. | 426/607 |
| 5,275,835 | 1/1994 | Masterson et al. | 426/607 |
| 5,288,512 | 2/1994 | Seiden | 426/607 |
| 5,380,544 | 1/1995 | Klemann et al. | 426/607 |

FOREIGN PATENT DOCUMENTS

| | | | |
|---|---|---|---|
| 60-53598 | 3/1985 | Japan | C11C 3/08 |
| WO93/15612 | 8/1993 | WIPO | A23D 9/00 |

OTHER PUBLICATIONS

J. C. Peters et al.; "Caprenin 3. Absorption and Caloric Value in Adult Humans"; *Journal of the American College of Toxicology*; pp. 357–367; vol. 10, No. 3, 1991.

*Primary Examiner*—Carolyn Paden
*Attorney, Agent, or Firm*—Tara M. Rosnell; Leonard Williamson; Rose Ann Dabek

[57] ABSTRACT

The present invention relates to reduced calorie fats comprising mixtures of reduced calorie triglycerides which are enriched in long chain fatty acid 2-position isomers (MLM triglycerides). In particular, the reduced calorie fats comprise at least about 40% of the long chain fatty acid 2-position isomer. The reduced calorie fats according to the present invention further comprise at least about 85% combined MML and MLM triglycerides, no more than about 5% combined LLM and LML triglycerides, no more than about 2% LLL triglycerides, no more than about 4% MMM triglycerides and no more than about 6% other triglycerides; wherein M=fatty acids selected from the group consisting of $C_6$ to $C_{10}$ saturated fatty acids, and mixtures thereof, and L=fatty acids selected from the group consisting of $C_{17}$ to $C_{26}$ saturated fatty acids, and mixtures thereof. The reduced calorie fats of the present invention have the following fatty acid composition by weight percent:

(a) from about 15% to about 70% $C_6$ to $C_{10}$ saturated fatty acids;

(b) from about 10% to about 70% $C_{17}$ to $C_{26}$ saturated fatty acids;

(c) not more than about 10% fatty acids selected from the group consisting of $C_{12:0}$ and $C_{14:0}$, and mixtures thereof;

(d) not more than about 20% fatty acids selected from the group consisting of $C_{18:1}$, $C_{18:2}$, $C_{18:3}$ and mixtures thereof, and (e) not more than 4% $C_{18:2}$ fatty acids.

The reduced calorie fats of the present invention exhibit rapid crystallization into the stable beta phase.

18 Claims, No Drawings

REDUCED CALORIE FATS WHICH COMPRISE REDUCED CALORIE TRIGLYCERIDES CONTAINING MEDIUM AND LONG CHAIN FATTY ACIDS AND WHICH EXHIBIT RAPID CRYSTALLIZATION TO BETA PHASE

TECHNICAL FIELD

The present invention relates to reduced calorie fats comprising reduced calorie triiglycerides containing medium and long chain fatty acids. The reduced calorie fats of the present invention exhibit rapid crystallization into the stable beta phase. These reduced calorie fat compositions are useful as replacements for conventional triglycerides in food products.

BACKGROUND OF THE INVENTION

Reduced calorie fats which are made from triglycerides containing medium and long chain fatty acids have been disclosed for use as a replacement for conventional triglyceride fats in food products. See, for example, Seiden; U.S. Pat. No. 5,288,512; Issued Feb. 22, 1994 which discloses reduced fat compositions comprising at least about 15% by weight triglycerides selected from the group MML, MLM, LLM and LML triglycerides and mixtures thereof; wherein M=fatty acids selected from the group consisting of $C_6$ to $C_{10}$ saturated fatty acids, and mixtures thereof, and L=fatty acids selected from the group consisting of $C_{17}$ to $C_{26}$ saturated fatty acids, and mixtures thereof, and wherein the fat has the following fatty acid composition by weight percent:

(a) from about 15% to about 70% $C_6$ to $C_{10}$ saturated fatty acids;

(b) from about 10% to about 70% $C_{17}$ to $C_{26}$ saturated fatty acids;

(c) not more than about 10% fatty acids selected from the group consisting of $C_{12:0}$ and $C_{14:0}$, and mixtures thereof, (d) not more than about 20% fatty acids selected from the group consisting of $C_{18:1}$, $C_{18:2}$, $C_{18:3}$ and mixtures thereof, and (e) not more than 4% $C_{18:2}$ fatty acids.

Seiden taught that the reduced calorie fats disclosed therein could be prepared by a wide variety of techniques such as by random rearrangement of long chain triglycerides and medium chain triglycerides, esterification of glycerol with a blend of the corresponding fatty acids, transesterification of a blend of medium and long chain fatty acid methyl esters with glycerol and transesterification of long chain fatty acid glycerol esters with medium chain triglycerides. Processes for preparing reduced calorie fats such as those disclosed in Seiden et al are also described, for example, in U.S. Pat. No. 5,142,071 to Kluesener et ai; Issued Aug. 25, 1992 and U.S. Pat. No. 5,142,072 to Stipp et al; issued Aug. 25, 1992.

Unfortunately, reduced calorie fats prepared according to these prior processes are slower to crystallize to the thermodynamically stable beta structure than conventional triglycerides. It has now been found that the rate of crystallization of reduced calorie fats containing reduced calorie triglycerides is dependent on the distribution of MML and MLM triglycerides present in the reduced calorie fat. Reduced calorie fats prepared according to prior processes typically contain less than about 40% of the MLM long chain fatty acid 2-position isomers. It has now been found that, surprisingly, reduced calorie fats comprising mixtures of reduced calorie triglycerides which are enriched in MLM long chain fatty acid 2-position isomers (e.g., which contain at least about 40% of the long chain fatty acid 2-position isomers) exhibit rapid crystallization into the stable beta phase (as measured by x-ray diffraction analysis and by differential scanning calorimetry) compared to reduced calorie fats comprising mixtures of reduced calorie triglycerides which contain less than about 40% of the long chain fatty acid 2-position isomer. In particular the amount of time required for the reduced fat to crystallize into the stable beta phase can be reduced from about 24 hours for a reduced calorie fat having a random distribution of MLM and MML triglyceride to almost instantaneous for reduced calorie fats comprising 100% MLM triglycerides.

It has also now been found that reduced calorie which are enriched in the MLM long chain fatty acid 2-position isomer are more resistant to thermal stress, more bloom stable, exhibit greater compatibility with other fats and fat isomers and have more desirable melting points than reduced calorie fats comprising mixtures of reduced calorie triglycerides which contain less than about 40% of the long chain fatty acid 2-position isomer.

SUMMARY OF THE INVENTION

The present invention relates to reduced calorie fats comprising mixtures of reduced calorie triglycerides which are enriched in long chain fatty acid 2-position isomers (MLM triglycerides). In particular, the reduced calorie fats comprise at least about 40% of the long chain fatty acid 2-position isomer. The reduced calorie fats according to the present invention further comprise at least about 85% combined MML and MLM triglycerides, no more than about 5% combined LLM and LML triglycerides, no more than about 2% LLL triglycerides, no more than about 4% MMM triglycerides and no more than about 6% other triglycerides; wherein M=fatty acids selected from the group consisting of $C_6$ to $C_{10}$ saturated fatty acids, and mixtures thereof, and L=fatty acids selected from the group consisting of $C_{17}$ to $C_{26}$ saturated fatty acids, and mixtures thereof. The reduced calorie fats of the present invention have the following fatty acid composition by weight percent:

(a) from about 15% to about 70% $C_6$ to $C_{10}$ saturated fatty acids;

(b) from about 10% to about 70% $C_{17}$ to $C_{26}$ saturated fatty acids;

(c) not more than about 10% fatty acids selected from the group consisting of $C_{12:0}$ and $C_{14:0}$, and mixtures thereof, (d) not more than about 20% fatty acids selected from the group consisting of $C_{18:1}$, $C_{18:2}$, $C_{18:3}$ and mixtures thereof, and (e) not more than 4% $C_{18:2}$ fatty acids.

The reduced calorie fats of the present invention exhibit rapid crystallization into the stable beta phase.

DETAILED DESCRIPTION OF THE INVENTION

The present invention relates to reduced calorie fats comprising mixtures of reduced calorie triglycerides which are enriched in long chain fatty acid 2-position isomers (MLM triglycerides). It has now been found that, surprisingly, reduced calorie fats comprising mixtures of reduced calorie triglycerides which are enriched in MLM long chain fatty acid 2-position isomers (e.g., which contain at least about 40% of the long chain fatty acid 2-position isomers) exhibit rapid crystallization into the alpha crystalline phase and rapid transformation to beta phase compared to reduced calorie fats comprising mixtures of reduced calorie triglycerides which contain less than about 40% of the long chain fatty acid 2-position isomer. The polymorphic phases, and particularly the beta phase referred to herein, are crystalline fat phases well known to those skilled in the art of fat X-ray crystallography. See Wille et al. "Polymorphism of Cocoa Butter," J. Am. Oil Chem., Vol. 43 (1966), pp. 491–96, which describes the six crystalline fat phases of cocoa butter. The reduced calorie fats of the present invention are described in detail as follows:

A. Description of the Reduced Calorie Fats

The reduced calorie fats of the present invention comprise:

(a) at least about 40% by weight MLM triglycerides;

(b) at least about 85% combined MLM and MML triglycerides;

(c) no more than about 5% combined LLM and LML triglycerides;

(d) no more than about 2% LLL triglycerides;

(e) no more than about 4% MMM triglycerides; and (f) no more than about 6% other triglycerides;

wherein M=fatty acids selected from the group consisting of $C_6$ to $C_{10}$ saturated fatty acids, and mixtures thereof, and L=fatty acids selected from the group consisting of $C_{17}$ to $C_{26}$ saturated fatty acids, and mixtures thereof.

By "medium chain fatty acids" is meant $C_{6:0}$ (caproic), $C_{8:0}$ (caprylic), or $C_{10:0}$ (capric) fatty acids or mixtures thereof. The $C_7$ and $C_9$ saturated fatty acids are not commonly found, but are not excluded from the possible medium chain fatty acids. The present medium chain fatty acids do not include lauric acid ($C_{12:0}$), sometimes referred to in the art as a medium chain fatty acid.

By "long chain fatty acids" is meant $C_{17:0}$ (margaric), $C_{18:0}$ (stearic), $C_{19:0}$ (nonadecylic), $C_{20:0}$ (arachidic), $C_{21:0}$ (heneicosanoic), $C_{22:0}$ (behenic), $C_{23:0}$ (tricosanoic), $C_{24:0}$ (lignoceric), $C_{25:0}$ (pentacosanoic), or $C_{26:0}$ (cerotic) fatty acids, or mixtures thereof.

As used herein, "MML" triglycerides are those triglycerides which contain a long chain fatty acid residue in the #1 or #3 position on the glycerol backbone and two medium chain fatty acid residues in the remaining two positions. Similarly, "LLM" triglycerides are those triglycerides which contain a medium chain fatty acid residue in the #1 or #3 position on the glycerol backbone and two long chain fatty acid residues in the remaining two positions, "LML" triglycerides are those triglycerides which contain a medium chain fatty acid residue in the #2 position and two long chain fatty acid residues in the #1 and #3 positions and "MLM" triglycerides are those triglycerides which contain a long chain fatty acid residue in the #2 position on the glycerol backbone and two medium chain fatty acid residues in the remaining two positions. "LLL" triglycerides are those triglycerides which contain 3 long chain fatty acid residues on the glycerol backbone and "MMM" triglycerides are those triglycerides which contain 3 medium chain fatty acid residues on the glycerol backbone. As used herein the term "other triglycerides" refers to triglycerides other than MML, MLM, LML, LLM, LLL, and MMM. MLM triglycerides are also referred to herein as long chain fatty acid 2-position isomers.

One key element of the reduced calorie fats of the present invention is that they contain at least about 40% of the MLM long chain fatty acid 2-position isomer. Preferably, the reduced calorie fats of the present invention contain at least about 45% MLM triglycerides, more preferably at least about 60% MLM triglycerides, and most preferably at least about 80% MLM triglycerides. In general, the higher the level of MLM triglycerides comprising the reduced calorie fat, the faster the rate of crystallization of the fat into the desired beta phase. Typically, a reduced calorie fat according to the present invention which contains at least about 40% MLM triglycerides will crystallize into the desired beta phase in less than about 8 hours, preferably less than about 4 hours, more preferably less than about 2 hours, even more preferably less than about 60 minutes, and most preferably less than about 30 minutes. Reduced calorie fats of the present invention have a melting point ranging from about 28° C. to about 60° C., preferably from about 31 ° C. to about 45° C., more preferably from about 31° C. to about 40° C., as measured by the differential scanning calorimetry method described hereinafter in the Analytical Methods section.

The reduced calorie fats according to the present invention further comprise at least about 85% combined MML and MLM triglycerides, preferably at least about 90% combined MML and MLM triglycerides, most preferably at least about 94% combined MML and MLM triglycerides. The reduced calorie fats of the present invention also comprise no more than about 5% by weight combined LLM and LML triglycerides, preferably no more than about 3% by weight combined LLM and LML triglycerides, more preferably no more than about 1% by weight combined LLM and LML triglycerides, and most preferably no more than about 0.5% by weight combined LLM and LML triglycerides. The reduced calorie fats of the present invention typically contain no more than about 2%, preferably no more than about 1% LLL triglycerides, and no more than about 4%, preferably no more than about 2%, most preferably no more than about 1% MMM triglycerides. The reduced calorie fats of the present invention further comprise no more than about 6%, preferably no more than about 4%, and most preferably no more than about 2% other triglycerides.

The reduced calorie fats of the present invention have the following fatty acid composition by weight percent:

(a) from about 15% to about 70% $C_6$ to $C_{10}$ saturated fatty acids;

(b) from about 10% to about 70% $C_{17}$ to $C_{26}$ saturated fatty acids;

(c) not more than about 10% fatty acids selected from the group consisting of $C_{12:0}$ and $C_{14:0}$, and mixtures thereof;

(d) not more than about 20% fatty acids selected from the group consisting of $C_{18:1}$, 1, $C_{18:2}$, $C_{18:3}$ and mixtures thereof; and (e) not more than 4% $C_{18:2}$ fatty acids.

In a preferred embodiment of the present invention, the medium chain fatty acids present in the reduced calorie fats comprise from about 35% to about 60%, preferably from about 40% to about 60% combined $C_8$ and $C_{10}$ saturated fatty acid. Preferably, the molar ratio of $C_8$ to $C_{10}$ saturated fatty acids in these reduced calorie fats ranges from about 30:70 to about 70:30, more preferably from about 40:60 to about 60:40.

The reduced calorie fats of the present invention can contain limited amounts of other fatty acids besides medium and long chain fatty acids, without losing the benefits of the invention. As indicated above, small amounts of $C_{12:0}$, $C_{14:0}$, $C_{18:1}$, $C_{18:2}$ and $C_{18:3}$ can be present.

Palmitic acids ($C_{16:0}$) is about 95% absorbed by the body, while the longer chain fatty acids are less absorbed. Therefore, it is preferred that the present reduced calorie fats contain not more than about 10% by weight $C_{16:0}$ fatty acid.

In another preferred embodiment, the reduced calorie fat will contain not more than about 6% by weight fatty acids selected from the group consisting of $C_{18:1}$, $C_{18:2}$, $C_{18:3}$, and mixtures thereof, more preferably not more than about 1%, most preferably not more than about 0.5%. Preferred reduced calorie fats also contain not more than 3%, and more preferably not more than about 1% by weight fatty acids selected from the group consisting of $C_{12:0}$ (lauric) and $C_{14:0}$ (myristic), and mixtures thereof. Lauric and myristic result in more fat deposition than medium chain fatty acids.

Preferred reduced calorie fats according to the present invention have the following preferred and most preferred carbon number profiles (CNP):

| CNP | PREFERRED (%) | MOST PREFERRED (%) |
| --- | --- | --- |
| 32 or lower | <3 | <1 |
| 34 | <2 | <1 |
| 36 | <4 | <2 |
| 38 | 15–40 | 15–30 |
| 40 | 35–60 | 45–55 |
| 42 | 15–35 | 20–30 |
| 44 | <2 | <1 |
| 46 | <1 | <0.6 |
| 48 | <0.8 | <0.6 |
| 50 | <0.6 | <0.5 |
| 52 | <0.4 | <0.3 |
| 54 or higher | <0.9 | 0.4 |

Table 1 below illustrates some of the possible triglyceride variations within the MML/MLM and LLM/LML groups. Combinations of different medium and long chain fatty acids on the triglycerides are correlated with the carbon numbers of the triglycerides. (The list is not meant to be exhaustive). The table shows that a wide variety of triglycerides exist at a given carbon number (CNP).

TABLE I

Some of the Possible Triglycerides of Saturated Medium* and Saturated Long Chain** Fatty Acids

MLM & LMM

| CNP | | | | | | |
| --- | --- | --- | --- | --- | --- | --- |
| 34 | 8-8-18 | 6-8-20 | 6-6-22 | 8-10-16 | | |
| | 8-18-8 | 6-20-8 | 6-22-6 | 8-16-10 | | |
| | | 8-6-20 | | 10-8-16 | | |
| 36 | 8-10-18 | 8-8-20 | 6-10-20 | 6-8-22 | 6-6-24 | 10-10-16 |
| | 8-18-10 | 8-20-8 | 6-20-10 | 6-22-8 | 6-24-6 | 10-16-10 |
| | 10-8-18 | | 10-6-20 | 8-6-22 | | |
| 38 | 10-10-18 | 8-10-20 | 8-8-22 | 8-6-24 | 6-10-22 | 6-12-20 |
| | 10-18-10 | 8-20-10 | 8-22-8 | 8-24-6 | 6-22-10 | 12-6-20 |
| | | 10-8-20 | | 6-8-24 | 10-6-22 | |
| 40 | 8-10-22 | 10-10-20 | 8-8-24 | 6-10-24 | | |
| | 8-22-10 | 10-20-10 | 8-24-8 | 6-24-10 | | |
| | 10-8-22 | | | 10-6-24 | | |
| 42 | 10-10-22 | 8-10-24 | | | | |
| | 10-22-10 | 8-24-10 | | | | |
| | | 10-8-24 | | | | |
| 44 | 10-10-24 | | | | | |
| | 10-24-10 | | | | | |

LLM & LML

| | | |
| --- | --- | --- |
| 38 | 6-16-16 | |

TABLE I-continued

Some of the Possible Triglycerides of Saturated Medium* and Saturated Long Chain** Fatty Acids

| | | | | |
| --- | --- | --- | --- | --- |
| | 16-6-16 | | | |
| 40 | 6-16-18 | 8-16-16 | | |
| | 6-18-16 | 16-8-16 | | |
| | 16-6-18 | | | |
| 42 | 6-18-18 | 8-16-18 | | |
| | 18-6-18 | 8-18-16 | | |
| | | 16-8-18 | | |
| 44 | 6-18-20 | 6-16-22 | 8-18-18 | |
| | 6-20-18 | 6-22-16 | 18-8-18 | |
| | 20-6-18 | 16-6-22 | | |
| 46 | 10-16-20 | 6-18-22 | 8-16-22 | |
| | 16-20-10 | 18-22-6 | 16-22-8 | |
| | 16-10-20 | 18-6-22 | 16-8-22 | |
| | 8-18-20 | 6-16-24 | 6-20-20 | 18-10-18 |
| | 18-20-8 | 16-24-6 | 20-6-20 | 18-18-10 |
| | 18-8-20 | 16-6-24 | | |
| 48 | 8-18-22 | 8-16-24 | 10-18-20 | |
| | 18-22-8 | 16-24-8 | 18-20-10 | |
| | 18-8-22 | 16-8-24 | 18-10-20 | |
| | 6-18-24 | 10-16-22 | 6-20-22 | |
| | 18-24-6 | 16-22-10 | 20-22-6 | |
| | 18-6-24 | 16-10-22 | 20-6-22 | |
| 50 | 8-20-22 | 10-18-22 | 6-22-22 | |
| | 20-22-8 | 18-22-10 | 22-6-22 | |
| | 20-8-22 | 18-10-22 | | |
| | 10-16-24 | 6-20-24 | 8-18-24 | |
| | 16-24-10 | 20-24-6 | 18-24-8 | |
| | 16-10-24 | 20-6-24 | 18-8-24 | |
| 52 | 10-20-22 | 10-18-24 | 8-22-22 | |
| | 20-22-10 | 18-24-10 | 22-8-22 | |
| | 20-10-22 | 18-10-24 | | |
| | 6-22-24 | 8-20-24 | | |
| | 22-24-6 | 20-24-8 | | |
| | 22-6-24 | 20-8-24 | | |

*Saturated medium chain fatty acids (M) chain lengths: 6, 8, 10.
**Saturated long chain fatty acids (L) chain length: 16, 18, 20, 22, 24. (While palmitic acid (C16) is included here as a long chain fatty acid for illustration purposes, it is not within the claim definition of a long chain fatty acid.)

The carbon number profile of the reduced calorie fats prepared according to the process of the present invention is such that from about 40% to 100% of the triglycerides having a carbon number of 42 are long chain fatty acid 2-position isomers. Preferably from about 45% to 100% of the triglycerides having a carbon number of 42 are long chain fatty acid 2-position isomers, and most preferably from about 60% to 100% of the triglycerides having a carbon number of 42 are long chain fatty acid 2-position isomers.

Mono-long chain triglycerides according to the present invention are preferred over di-long chain triglycerides. Molecular distillation can separate MML/MLM from LLM/LML-type triglycerides, and can shift the composition in carbon number concentration, but it cannot fractionate the triglycerides according to their carbon numbers. Because the composition greatly affects the melting point of triglycerides, fractionation by molecular distillation is an important tool.

Non-solvent or solvent crystal fractionation can also fractionate LMM/MLM-type triglycerides from the higher melting LLM/LML triglycerides. Crystallization and filtration are usually repeated two or three times. Fractional solvent crystallization or liquid/liquid extraction can also be used to enrich desired MLM isomer levels.

B. Uses of the Reduced Calorie Fats of the Present Invention

The reduced calorie fats of the present invention can be used as a partial or total replacement for normal triglyceride fat in any fat-containing food composition comprising fat and nonfat ingredients to provide reduced calorie benefits. In order to obtain a significant reduction in calories, it is necessary that at least about 50% of the total fat in the food composition, or at least about 20% of the caloric value of the food, comprise the reduced calorie fat. On the other hand, very low calorie and thus highly desirable food compositions of the invention are obtained when the total fat comprises up to 100% of the reduced calorie fat of this invention, and up to about 50% of the calories.

The present reduced calorie fats are useful in a wide variety of food and beverage products. For example, the fats can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked goods, pizzas and pizza crusts, baked farinaceous snack foods, and other baked salted snacks.

In addition to their uses in baked goods, the reduced calorie fats can be used alone or in combination with other regular calorie fats and oils to make shortening and oil products. Suitable sources of regular fats and oils include, but are not limited to: 1) vegetable fats and oils such as soybean, corn, sunflower, rapeseed, low erucic acid rapeseed, canola, cottonseed, olive, safflower, and sesame seed; 2) meat fats such as tallow or lard; 3) marine oils; 4) nut fats and oils such as coconut, palm, palm kernel, or peanut; 5) milkfat; 6) cocoa butter and cocoa butter substitutes such as shea, or illipe butter; and 7) synthetic fats. Shortening and oil products include, but are not limited to, shortenings, margarines, spreads, butter blends, lards, salad oils, popcorn oils, salad dressings, mayonnaise, and other edible oils.

Certain of the present reduced calorie fats are especially useful in flavored confectionery compositions, particularly chocolate-flavored confectionery compositions. See U.S. application entitled "Process for Tempering Flavored Confectionery Compositions Containing Reduced Calorie Fats and Resulting Tempered Products" to Albert M. Ehrman, Paul Seiden, Rose M. Weitzel and Robert L. White, Ser. No. 329,619 (P&G Case 3948), filed Mar. 28, 1989 now U.S. Pat. No. 4,888,196, which is incorporated by reference.

The present reduced calorie fats can also be fortified with vitamins and minerals, particularly the fat-soluble vitamins. U.S. Pat. No. 4,034,083 of Mattson (incorporated by reference herein) discloses polyol fatty acid polyesters fortified with fat-soluble vitamins. The fat-soluble vitamins include vitamin A, vitamin D, vitamin E, and vitamin K. Vitamin A is a fat-soluble alcohol of the formula $C_{20}H_{29}OH$. Natural vitamin A is usually found esterified with a fatty acid; metabolically active forms of vitamin A also include the corresponding aldehyde and acid. Vitamin D is a fat-soluble vitamin well known for use in the treatment and prevention of tickets and other skeletal disorders. Vitamin D comprises sterols, and there are at least 11 sterols with vitamin D-type activity. Vitamin E (tocopherol) is a third fat-soluble vitamin which can be used in the present invention. Four different tocopherols have been identified (alpha, beta, gamma and delta), all of which are oily, yellow liquids, insoluble in water but soluble in fats and oils. Vitamin K exists in at least three forms, all belonging to the group of chemical compounds known as quinones. The naturally occurring fat-soluble vitamins are $K_1$ (phylloquinone), $K_2$ (menaquinone), and $K_3$ (menadione). The amount of the fat-soluble vitamins employed herein to fortify the present reduced calorie fat materials can vary. If desired, the reduced calorie fats can be fortified with a recommended daily allowance (RDA), or increment or multiple of an RDA, of any of the fat-soluble vitamins or combinations thereof.

Vitamins that are nonsoluble in fat can similarly be included in the present reduced calorie fats. Among these vitamins are the vitamin B complex vitamins, vitamin C, vitamin G, vitamin H, and vitamin P. The minerals include the wide variety of minerals known to be useful in the diet, such as calcium, magnesium, and zinc. Any combination of vitamins and minerals can be used in the present reduced calorie fat.

The present reduced calorie fats are particularly useful in combination with particular classes of food and beverage ingredients. For example, an extra calorie reduction benefit is achieved when the fat is used with noncaloric or reduced calorie sweeteners alone or in combination with bulking agents. Noncaloric or reduced calorie sweeteners include, but are not limited to, aspartame; saccharin; alitame, thaumatin: dihydrochalcones: cyclamates; steviosides; glycyrrhizins, synthetic alkoxy aromatics, such as Dulcin and P-4000: sucrolose: suosan; miraculin; monellin; sorbitol, xylitol: talin: cyciohexylsulfamates; substituted imidazolines; synthetic sulfamic acids such as acesulfame, acesulfam-K and n-substituted sulfamie acids; oximes such as perilartine; rebaudioside-A: peptides such as aspartyl malonates and succanilic acids; dipeptides: amino acid based sweeteners such as gem-diaminoalkanes, meta-aminobenzoic acid, L-aminodicarboxylic acid alkanes, and amides of certain alpha-aminodicarboxylic acids and gem-diamines: and 3-hydroxy-4-alkyloxyphenyl aliphatic carboxylates or heterocyclic aromatic carboxylates.

The reduced calorie fats can be used in combination with other noncaloric or reduced calorie fats, such as branched chain fatty acid triglycerides, triglycerol ethers, polycarboxylic acid esters, sucrose polyethers, neopentyl alcohol esters, silicone oils/siloxanes, and dicarboxylic acid esters. Other partial fat replacements useful in combination with the reduced calorie fats are medium chain triglycerides, highly esterified polyglycerol esters, acetin fats, plant sterol esters, polyoxyethylene esters, jojoba esters, mono/diglycerides of fatty acids, and mono/diglycerides of short-chain dibasic acids.

Certain of the present reduced calorie fats are particularly useful in reduced calorie fat compositions comprising certain substantially nonabsorbable, substantially nondigestible polyol polyesters. See U.S. application entitled "Reduced Calorie Fat Compositions Containing Polyol Polyesters and Reduced Calorie Triglycerides" to Paul Seiden, Corey J. Kenneally and Thomas J. Wehmeier, Serial No. 329,629 (P&G Case 3947), filed Mar. 28, 1989, now abandoned, which is incorporated by reference.

Food products can comprise these reduced calorie fat compositions as the sole fat ingredient, or in combination with other fat ingredients such as triglyceride oils. These food products include frying oils for salted snacks and other fried foods, firm chocolate-flavored products such as chocolate-flavored candy bars or chips, as well as cooking and salad oils that are clear at room temperature, i.e., about 70° F. (21.1° C.), and preferably at lower temperatures, e.g., at about 50° F. (10° C.).

Surprisingly, certain of the present reduced calorie fats can function as anti-anal leakage agents for the polyol polyesters. In addition, the combination of the polyol polyesters with these reduced calorie fats provides significant advantages over the use of either component alone. The advantages provided by these combinations include: (1) increased caloric reduction; (2) textural/taste benefits (e.g., less waxiness/greasiness, improved mouthmelt); (3) less color degradation during frying; and (4) less high temperature volatility and foaming during frying.

Bulking or bodying agents are useful in combination with the reduced calorie fats in many food compositions. The bulking agents can be nondigestible carbohydrates, for example, polydextrose and cellulose or cellulose derivatives, such as carboxymethylcellulose, carboxyethylcellulose, hydroxypropylcellulose, methylcellulose and microcrystalline cellulose. Other suitable bulking agents include gums (hydrocolloids), starches, dextrins, fermented whey, tofu, maltodextrins, polyols, including sugar alcohols, e.g. sorbitol and mannitol, carbohydrates, e.g. lactose, and 5-C hydroxy methyl aldose compounds (see Mazur et al., European Patent Applications 341,062 and 341,063).

Similarly, food and beverage compositions can be made that combine the present reduced calorie fats with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

These dietary fibers may be in a crude or purified form. The dietary fiber used may be of a single type (e.g. cellulose), a composite dietary fiber (e.g. citrus albedo fiber containing cellulose and pectin), or some combination of fibers (e.g. cellulose and a gum). The fibers can be processed by methods known to the art.

The reduced calorie fats can also contain minor amounts of optional flavorings, emulsifiers, anti-spattering agents, anti-sticking agents, anti-oxidants, or the like.

Of course, judgment should be exercised to make use of appropriate reduced calorie fats and combinations of these fats with other food ingredients. For example, a combination of sweetener and fat would not be used where the specific benefits of the two are not desired. The fat and fat ingredient combinations are used where appropriate, and in the proper amounts.

Many benefits are obtained from the use of the present reduced calorie fats in food and beverage compositions, either when used alone or in combination with the ingredients discussed above. A primary benefit is the calorie reduction achieved when the fat is used as a total or partial fat replacement. This calorie reduction can be increased by using combinations of the present fats with reduced calorie sweeteners, bulking agents, or other reduced calorie or noncaloric fats. Another benefit which follows from this use is a decrease in the total amount of fats in the diet.

A related benefit is that the use of the reduced calorie fats allows the production of foods and beverages that are stable in terms of shelf stability and penetration stability. Compositions made with the reduced calorie fats have acceptable organoleptic properties, particularly taste and texture.

Dietary foods can be made with the reduced calorie fats to meet special dietary needs, for example, of persons who are obese, diabetic, or hypercholesterolemic. The reduced calorie fat can be a major part of a low-fat, low-calorie, low-cholesterol diet, and they can be used alone or in combination with drug therapy or other therapy. Combinations of food or beverage products made with the reduced calorie fat can be used as part of a total dietary management regimen, based on one or more of these products, containing the reduced calorie fat alone or in combination with one or more of the above-mentioned ingredients, to provide one or more of the above-mentioned benefits.

This discussion of the reduced calorie fats uses, combinations, and benefits, is not intended to be limiting or all-inclusive. It is contemplated that other similar uses and benefits can be found that will fall within the spirit and scope of this invention.

C. Method of Preparation

In a preferred method for preparing the reduced calorie fats of the present invention, an at least about 60% pure $C_{18}$–$C_{24}$ long chain fatty acid monoglyceride or mixture thereof is esterified with an at least about 90% pure $C_6$–$C_{10}$ medium chain fatty acid or mixture thereof at a temperature of from about 225° to about 350° C. and at a pressure of from about 200 to about 2000 mmHg in the substantial absence of an esterification catalyst. The mole ratio of fatty acid to monoglyceride used in this monoglyceride esterification is at least about 3:1. Water generated during this monoglyceride esterification is continuously removed.

The medium chain fatty acids used to prepare the reduced calorie fats of the present invention can be derived from a number of different sources. For example, medium chain saturated fatty acids can be obtained from coconut, palm kernel or babassu oils. They can also be obtained from commercial medium chain triglycerides, such as the Captex 300 brands sold by Capital City Products of Columbus, Ohio. Typically, these sources of medium chain fatty acids are subjected to hydrolysis to provide a mixture of free fatty acids, followed by thermal distillation to provide a fatty acid fraction enriched in the medium chain fatty acids. It is also desirable that the sources of medium chain fatty acids have good thermal color stability, e.g., after heating at 205° C. for 2 hours, a mixture of $C_8$ and $C_{10}$ saturated fatty acids has only a 5–10% optical transmission reduction when measured at 440/550 nanometers.

The source of medium chain fatty acids used to prepare the reduced calorie fats of the present invention needs to be of sufficiently high purity to provide the desired level of MML/MLM triglycerides. Generally the source of medium chain fatty acids is at least about 90% pure in medium chain fatty acids, and is preferably at least about 95% pure, in such fatty acids. Preferably, the source of medium chain fatty acids comprises $C_8$ saturated fatty acid, $C_{10}$ saturated fatty acid, or a mixture of $C_8$ and $C_{10}$ saturated fatty acids. The weight ratio of $C_8$ to $C_{10}$ saturated fatty acids is preferably in the range of from about 30:70 to about 70:30.

The long chain (i.e., $C_{18}$–$C_{24}$) fatty acid monoglycerides used herein can be prepared by a wide variety of techniques. These techniques include:

(a) Esterification or transesterification of glycerol acetone or glycidol with the respective long chain fatty acid(s), or long chain fatty acid lower alkyl (e.g., methyl or ethyl) ester(s), followed by hydrolysis of the respective blocking group. See Hartman, "Preparation of alpha.-

Monoglycerides by a Modified Isopropylidene-Glycerol Method," *Chemistry and Industry* (Jun. 18, 1960), pp. 711–12 (herein incorporated by reference), which discloses the preparation of 1-monoglycerides by the use of the modified isopropylidene-glycerol method, and Mattson et al, "Synthesis and Properties of Glycerides," *J. Lipid Res.*, Vol. 3, No. 3 (1962), pp. 281–96 (herein incorporated), which discloses the same method. See also U.S. Pat. No. 3,595,888 to Reiser et al, issued Jul. 27, 1971, and U.S. Pat. No. 3,251,870 to Dalby, issued May 17, 1966 (herein incorporated by reference) which disclose isopropylidene-glycerol and glycidol methods for synthesizing monoglycerides.

(b) Esterification or transesterification of glycerol with the respective long chain fatty acid(s), or long chain fatty acid lower alkyl ester(s), optionally using strong base esterification catalysts such as sodium hydroxide or sodium methoxide, or strong acid esterification catalysts such as hydrogen fluoride, perchloric acid, phosphoric acid or p-toluenesulfonic acid. See Choudhury, "The Preparation and Purification of Monoglycerides: Direct Esterification of Fatty Acids with Glycerol", *J. Am. Oil Chem. Soc.* Vol. 39 (1962), pp. 345–47 (herein incorporated by reference), which discloses the preparation of monoglycerides by esterification of glycerol with various fatty acids (e.g. stearic acid), optionally using sodium hydroxide as the catalyst. See also U.S. Pat. No. 3,551,464 to Miller et al, issued Dec. 29, 1970 (herein incorporated by reference), which discloses the preparation of monoglycerides from long chain aliphatic acids and esters that are esterified or transesterified with glycerol using hydrogen fluoride as the catalyst.

(c) Hydrolysis of a naturally occurring oil, preferably a completely or substantially completely hydrogenated naturally occurring oil (e.g., high erucic acid rapeseed oil or soybean oil hydrogenated to an Iodine Value (I.V.) of about 10 or less) by the use of a 1,3-specific lipase, followed by removal of the residual fatty acids, glycerol, diglycerides and triglycerides. See Holmberg, "Enzymatic Preparation of Monoglycerides in Microemulsion," *J. Am. Oil Chem. Soc.*, Vol. 65 (1988), pp. 1544–48, which is incorporated by reference.

(d) Esterification or transesterification of glycerol with the respective long chain fatty acid(s) or long chain fatty acid lower alkyl ester(s) using a monoglyceride lipase (e.g., Ammano Pharmaceutical type G), followed by purification. See European patent application 191,217 to Yamaguchi et al, published Aug. 20, 1986, which is incorporated by reference.

(e) Glycerolysis of naturally occurring oils, preferably completely or substantially completely hydrogenated naturally occurring oils. See Choudhury, "The Preparation and Purification of Monoglycerides; Glycerolysis of Oils", *J. Am. Oil Chem. Soc.*, Vol. 37 (1960), pp. 483–86, and Feuge et ai, "Modification of Vegetable Oils: The Practical Preparation of Mono- and Diglycerides," *Oil and Soap,* (August, 1946), pp. 259–64, which are incorporated by reference.

The long chain fatty acids per se or naturally occurring fats and oils can serve as sources of the long chain fatty acids. For example, soybean oil and high erucic acid rapeseed oil hydrogenated to an I.V. of about 10 or less are good sources of stearic and behenic fatty acids, respectively. Odd chain length long chain fatty acids can be derived from certain marine oils. Alternatively, mixed chain length fatty acid monoglycerides can be fractionated to provide a source of long chain fatty acids. For example, hydrogenated high erucic acid rapeseed oil can be transesterified with glycerol to provide a mixture of long chain fatty acid monoglycerides which can be subsequently fractionated by liquid/liquid extraction or adsorptive separation to yield a monobehenin-enriched mixture. The source of long chain fatty acids usually needs to be of sufficiently high purity in order to provide monoglycerides suitable for the esterification process of the present invention. Usually, the source of long chain fatty acids is at least about 90% pure in long chain fatty acids, and is preferably at least about 95% pure in such fatty acids. Preferably, the purity is in the range of from about 90 to about 98% long chain fatty acids.

The source of the long chain fatty acid monoglycerides used to prepare the reduced calorie fats of the present invention needs to be of sufficiently high purity in order to provide the desired level of MML/MLM triglycerides. Generally, the source of these monoglycerides, needs to be at least about 60% pure in long chain fatty acid monoglycerides, and is preferably at least about 90% pure, most preferably at least about 95% pure, in such monoglycefides. Such purities can typically be achieved by purification of the crude source of monoglycerides by molecular distillation, fractional crystallization, liquid/liquid extraction or adsorptive separation, e.g., by weak acid ion exchange resins to remove various impurities, including unreacted long chain fatty acids and particularly, to decrease the level of dilong chain fatty acid diglycerides (LL) to about 3% or less. Residual glycerol present in the crude source of monoglycefides can be removed by settling, centrifugation, thermal distillation, or fractional crystallization to decrease the glycerol level to about 1% or less. In addition, it is desirable to minimize the formation of glycerol dehydration products (e.g., polyglycerols) to a level of about 1% or less.

The preferred source of monoglycerides for use in preparing the reduced calorie fats of the present invention is at least about 90%, and is preferably at least about 95%, pure monobehenin. This preferred monoglyceride can be obtained by hydrolysis of substantially completely hydrogenated (i.e., I.V. about 10 or less) high erucic acid rapeseed oil, thermal distillation of the resulting fatty acid mixture to provide a behenic fatty acid-enriched fraction, and then estefification of glycerol with this behenic acid-enriched fraction to provide a crude mixture of monoglycerides. This synthesis route minimizes the formation of base catalyzed by-products such as difatty ketones or diglycerols. This crude monoglycefide mixture can be subsequently purified by molecular distillation, solvent (e.g., ethyl alcohol) crystallization, liquid/liquid extraction or adsorption on a weak acid ion exchange resin to yield a source of monoglycerides having the desired purity of monobehenin.

In order to provide a mixture of MML/MLM triglycerides which is enriched in the long chain fatty acid 2-position isomer, it is important to use an excess of the medium chain fatty acids relative to the monoglycerides. Typically, the mole ratio of fatty acid to monoglyceride is in the range of from about 3:1 to about 24:1, with a preferred mole ratio in the range of from about 16:1 to about 18:1, i.e. a substantial excess.

An important aspect of the esterification process used to prepared the reduced calorie fats of the present invention is that it is typically carried out in a solvent-free system. At the temperatures at which the esterification process is carried out, the mixture of monoglycerides and medium chain fatty acids forms an essentially homogeneous melt. Accordingly, solvents are not required in carrying out the esterification process of the present invention.

Another important aspect of the esterification process used to prepare the reduced calorie fats of the present invention is that it is carried out in the substantial absence of an esterification catalyst. As used herein, the term "substantial absence of esterification catalyst" means that the esterification process of the present invention is carried out without intentionally adding such catalysts. Esterification catalysts such as strong bases (e.g. sodium hydroxide or sodium methoxide) and strong acids (e.g. phosphoric acid or p-toluenesulfonic acid) are not required in order to carry out the esterification process of the present invention. Indeed, it has been surprisingly found that strong acid esterification catalysts such as phosphoric acid or p-toluenesulfonic acid tend to promote undesired rearrangement of the resulting glycerides, thus decreasing the level of desired MML/MLM triglycerides. In addition to promoting undesired rearrangement, strong base esterification catalysts such as sodium methoxide have also been found to cause the formation of undesired di-fatty ketone by-products.

An especially important aspect of the esterification process used to prepare the reduced calorie fats of the present invention is the esterification temperature. Prior processes for the preparation of MML/MLM triglycerides taught that at esterification temperatures of from about 140° C. to about 250° C., the esterification of monoglycerides with medium chain fatty acids is favored over rearrangement of the long chain fatty acid residues attached to the glycefide due to hydrolysis/reesterification, so that MML/MLM triglycerides could be selectively made. Preferable esterification temperatures according to these prior processes ranged from about 140° C. to about 220° C.

Surprisingly, it has now been determined that, at esterification temperatures of from about 225° C. to about 350° C., preferably from about 225° C. to about 300° C., more preferably from about 225° C. to about 245° C., and most preferably from about 235° C. to about 245° C., MML/MLM triglycerides which are enriched in long chain fatty acid 2-positional isomers can be formed. In particular, the amount of 2-positional isomer in the reduced calorie fat can be increased by up to about 67% over prior reduced calorie fats when the esterification reaction is carried out at temperatures ranging from 225° C. to about 350° C. This is desirable since it has been found that triglycefide mixtures containing higher levels of MLM triglycerides crystallize into the desired beta phase at a much faster rate than triglyceride mixtures containing lower levels of MLM triglycerides.

A second especially important aspect of the process used to prepare the fats of the present invention is the pressure at which the selective esterification reaction is run. Prior processes were typically pan at pressures ranging from about 200 to about 760 mmHg. It has now been found, however, that MML/MLM triglycerides which are enriched in long chain fatty acid 2-positional isomers can be formed by running the estefification reation at pressures ranging from about 200 to about 2000 mmHg, preferably from about 700 to about 1750 mmHg, more preferably from about 700 to about 1520 mmHg.

Another important aspect of the esterification process used to prepare the fats of the present invention is the removal of water generated during the reaction of the medium chain fatty acids with the monoglycerides. It has been found that water generated during this reaction that remains in the reaction mixture can cause hydrolysis of the resulting glycefides, and therefore lead to undesired rearrangement that decreases the level of desired MML/MLM triglycerides. Accordingly, water that is generated during the reaction is continuously removed from the reaction mixture. Suitable methods for continuous removal of this generated water include vacuum stripping of the reaction mixture (e.g., at pressures of from 200 to about 700 mmHg), inert gas (e.g., nitrogen) sparging of the reaction mixture using high shear mixing with high gas velocities, adsorption by hydrophilic materials such as zeolite molecular sieves, activated carbon and activated alumina, or combinations of these techniques. For example, in the case of nitrogen gas sparging, 0.1 to 10 l./min. gas flow per liter of reaction mixture in conjunction with high shear mixing (e.g. a 5 to 600 m/min. tip speed) are preferred for removal of generated water. (This degree of high shear mixing is typically achieved by a drive motor energy input of 1.5 to 3 kilowatts per 1000 liters of reaction mixture.) In addition, it is preferred that the fatty acids and monoglyceride starting materials be essentially anhydrous (e.g. by vacuum dehydration) prior to esterification.

The esterification process can be carried out as either a batch or continuous reaction system. For example, mixed flow configuration can be used to continuously react the medium chain fatty acids with the monoglycerides in one or more reaction stages. It is preferred that the reaction system(s) be equipped with partial condensers to allow continuous reflux of the medium chain fatty acids while generated water is being removed. Alternatively, thin film-type reaction systems operated under vacuum at high temperatures with short residence times can be used in this esterification step. Typically, the solid or liquid monoglycerides are added to the melted medium chain fatty acids at the desired esterification temperature to permit more effective removal of generated water and to minimize disproportionation of the monoglycefides to diglycerides/glycerol, as well as the reaction of monoglycerides with medium and long chain (ML) diglycerides. The monoglycerides are also preferably added slowly to the melted fatty acids at a controlled rate of addition during esterification to minimize the concentration of unreacted monoglycerides in the mixture, and thus minimize the formation of MLL/LML triglycerides.

The particular reaction times for carrying out this estefification process can vary greatly depending upon the mole ratio of fatty acids to monoglycerides used, the particular esterification temperatures used, and the yield/degree of purity desired for the MML/MLM triglycerides. In general the reaction times for carrying out the esterification process of the present invention are less than the reaction times required for prior esterification processes. Usually, reaction times of from about 1 to about 6 hours are suitable for batch reaction systems. Preferably, the estefification process of the present invention is carried out for a period of from about 1 to about 3 hours, more preferably from about 1 to about 2 hours, in a batch reaction system. (Equivalent residence times can be used in continuous reaction systems.)

An important result of the esterification process used in the present invention is that at least 99% of the partial glycerides are convened to the respective triglycerides. Furthermore, the esterification process of the present invention can achieve very low diglyceride levels, e.g. diglyceride levels of about 1% or less. This makes the MML/MLM triglycerides obtained by the esterification process of the present invention particularly suitable for flavored confectionery fat products.

After the esterification process described hereinbefore has been carried out for the appropriate time, the level of desired MML/MLM triglycerides in the triglyceride fraction of the reaction mixture is usually at least about 55%, is typically at least about 80%, and is preferably at least about 90%. The level of MML/MLM triglycerides in this reaction mixture can be sufficiently high so that further purification is unnecessary, particularly depending upon the proposed use of the MML/MLM triglycerides. However, purification of the reaction mixture resulting from the esterification step is typically required in order to remove various components such as unreacted medium chain fatty acids, and, in particular, MMM and MLL/LML triglycerides. Purification can also significantly increase the level of MLM triglycerides in the reaction mixture. Subsequent purification can be carried out by a variety of techniques known in the art. See, for example, Kiuesener et al; U.S. Pat. No. 5,142,071; Issued Aug. 25, 1992, herein incorporated by reference.

In addition to the process hereinbefore described, reduced calorie fats which are enriched in MLM triglycerides can be prepared by the catalytic esterification of behenic anhydride and MM diglycerides. (See example 3 hereinafter. )

ANALYTICAL METHODS

A number of parameters used to characterize elements of the present invention are quantified by particular experimental analytical procedures. Each of these procedures is described in detail as follows:

1. Method for Measuring Level of Long Chain Fatty Acid 2-position Isomer Present in Reduced Calorie Fats This method is an application of high performance liquid chromatography (HPLC) using a reversed-phase column, non-aqueous eluent, and a laser light-scattering detector (LLSD) for the quantification of triglyceride positional isomers in the reduced calorie fats herein. The triglyceride peaks are separated by carbon number (molecular weight) and further resolved based on the position of the long chain fatty acid chain on the glycerol backbone. Thus each carbon number (CN) triglyceride appears as a doublet; the triglyceride with the long chain fatty acid in the middle (2-position) elutes prior to the triglyceride with the long chain fatty acid on the end (1,3-position). A high-efficiency column, low eluent flow rate, and subambient column temperature are needed for the separation of the isomers.

For quantification, reduced calorie fat samples are dissolved in isopropanol. Quantification is by area percent, normalized within a CN doublet.

| APPARATUS | |
|---|---|
| Liquid Chromatograph | Hewlett-Packard 1090, equipped with a ChemStation |
| Detector | Varex ELSD II evaporative light-scattering detector, Varex Corp., Burtonsville, MD. |
| Data Collection | Hewlett-Packard ChemStation |
| Circulating Bath | Fisher Scientific Isotemp Refrigerated Circulator Model 910, Fisher Scientific, 9403 Kenwood Rd., Suit C-208, Cincinnati, OH |
| Column Jacket | Glass with Teflon ferrules, custom-built at Procter & Gamble Glass Shop (Note: jacket must be glass, not acrylic, to accommodate the propylene glycol in the circulating bath) |
| Vials | 1 mL with Teflon/silicone septa |
| Column | E. Merck, LiChroCART, Superspher 100 RP-18, 25 cm × 4 mm i.d., 3 micron spherical particles, EM Separations, 480 Democrat Rd., Gribbstown, NJ. |
| Vacuum Filter Assembly | 300 mL glass funnel, glass base filter support, stainless steel filter support screen, TFE support screen gasket, aluminum clamp, one liter vacuum flask |
| Filters | Rainin Nylon-66 membrane filters, 0.45 micron pore size, 47 mm diameter, #38-114, Rainin Instrument Co., Inc., Woburn, MA |
| Analytical Balance | Mettler HK 160 |
| Volumetric Flasks | 10 mL |
| Calculator | Texas Instrument TI-55 III |
| REAGENTS | |
| Isopropanol (IPA) | HPLC grade |

REFERENCE STANDARDS

A working reference material (WRM) is used to verify proper operation of this method. The WRM is a batch of reduced calorie fat which has been analyzed at least 4 times to establish the mean and standard deviation for quantification of each of the isomers. The WRM is analyzed daily. If the result on the WRM is equal to or within ±3 standard deviations of the known value, then the equipment, reagents and operations are performing satisfactorily. If the result on the reference standard is outside ±3 standard deviations of the known value, then a rerun of the reference standard is started immediately. If the result on the rerun is equal to or within 3 standard deviations of the known value, then the equipment, reagents and operations are performing satisfactorily. If the rerun is outside the ±3 standard deviations of the known value, then the sample results shall be rejected and troubleshooting procedures begun.

Operation

Standards
The WRM solution should be fleshly prepared daily.
Mobile Phases
The eluent is HPLC-grade isopropanol (IPA), which should be filtered through a 0.45 micron filter prior to use.
Instrumental Conditions
1. Eluent is IPA.
2. Initial flow rate is 0.05 mL/min. This is held for 180 minutes, then flow is ramped to 0.15 mL/min. over one minute. The 0.15 mL/min. flow rate is held for 28 minutes, then the flow is ramped back down to 0.05 mL/min. over one minute.
3. Column temperature is 0° C.
4. Injection size is 20 microliters.
5. Integration is begun at 122 minutes, using a peak width of 2.50, a threshold of −10 and area reject of 1. Note that the chromatogram may be integrated manually if the operator deems the integration using these parameters to be unsatisfactory.
6. Detector temperature is 133° C., nitrogen flow rate through detector is set to 34 mm.

Daily Operation
1. Degas the eluent for ten minutes with helium sparging prior to turning on the pumps. Allow the detector to warm up during the initial ten minute sparge.
2. After the detector is warmed up, start the nitrogen flow through it. Load the data acquisition parameters and start the pump so solvent is flowing at 0.05 mL/min.
3. Turn on the circulating bath and set temperature for 0° C. Allow the bath to reach 0° C., then allow the column to equilibrate at 0.05 mL/min. and 0° C. for at least 60 minutes.

4. Prepare the WRM as follows:
   a. Melt the sample in a warm water bath; stir to ensure homogeneity.
   b. Weigh the melted sample into a 10 mL volumetric flask so that the final concentration in isopropanol will be between 4.5 and 8.8 mg/mL. Record weight to fourth decimal place.
   c. Dissolve sample in isopropanol and dilute to volume with isopropanol.
5. Inject the WRM and check for proper operation of the method by comparing the reported results for this standard with established results of this method. If the reference standard is within ±3 standard deviations of the established results, then the samples can be run.

Procedure

Sample Preparation

A. For reduced calorie fats containing the same number of major CN triglycerides as the WRM:
  Follow steps 4a–c for the preparation of the WRM.
B. For reduced calorie fats that are predominantly 1 carbon number:
  Follow steps 4a–c for the preparation of the WRM except weigh out enough sample so that the final concentration in isopropanol is between 2.5 and 4.0 mg/mL.
C. For reduced calorie fats containing large amounts of free medium chain fatty acids:
  For these samples, the approximate level of triglyceride in the sample must be known (as determined by another analytical method, such as a GC profile). Follow steps 4a–c for the preparation of the WRM except weigh enough of the homogeneous sample into the 10 mL volumetric flask so that the final concentration of triglyceride will be between 4.5 and 8.8 mg/mL. For example, if the sample contains only 20% triglyceride, then use five times as much sample as for a finished product reduced calorie fat sample.

WRM and Sample Analysis
  1. Load the flow rate program described under "Instrumental Conditions" hereinabove.
  2. Load the integration parameters described under "Instrumental Conditions" hereinabove.
  3. Inject the WRM and the samples.

Quantification

Quantification is by area percent within each carbon number doublet. Use the peaks of the WRM to assign peak identities in the sample. The first two major peaks at retention times of approximately 137 and 142 minutes are the CN38 2-position and 1,3-position isomers, the third and fourth major peaks at approximately 156 and 164 minutes are the CN40 2-position and 1,3-position isomers, and the fifth and sixth peaks at approximate retention times of 182 and 189 minutes are the CN42 2-position and 1,3 position isomers, respectively. Due to retention time shifts caused by temperature fluctuation and column aging, peak assignments must be made using the daily WRM chromatogram.

A sample calculation is shown below:

To calculate the percent of the CN38 that is 2-postion:

$$\% \text{ 2-position CN38} = \frac{\text{area 2-position CN38}}{\text{area 2-position CN38 + area 1,3-position CN38}} \times 100\%$$

2. Carbon Number Profile (CNP)

The carbon number profile (CNP) of the triglycerides (i.e. MML/MLM, MLL/LML, MMM and LLL) present in the reduced calorie fat can be determined by programmed temperature-gas chromatography (GC) using a short fused silica column coated with methyl silicone for analysis and characterization of the composition by molecular weight. The triglycerides are separated according to their respective carbon numbers, wherein the carbon number defines the total number of carbon atoms on the combined fatty acid residues. The carbon atoms on the glycerol molecule are not counted. Glycerides with the same carbon number will elute as the same peak. For example, a triglyceride composed of three $C_{16}$ (palmitic) fatty acid residues will co-elute with triglycerides made up of one $C_{14}$ (myristic), one $C_{16}$ and one $C_{18}$ (stearic) fatty acid residue or with a triglyceride composed of two $C_{14}$ fatty acid residues and one $C_{20}$ (arachidic) fatty acid residue. See Kluesener et al: U.S. Pat. No. 5,142,071; Issued Aug. 25, 1992, which is incorporated by reference.

3. Fatty Acid Composition
  Principle
  The fatty acid composition of the triglycerides comprising the reduced calorie fat of the present invention is measured by gas chromatography. First, fatty acid ethyl esters of the triglycerides are prepared by any standard method (e.g., by transesterification using sodium ethoxide), and then separated on a capillary column which is coated with DB-WAX stationary phase. The fatty acid ethyl esters are separated by chain length and degree of unsaturation. A split injection is made with flame ionization detection. Quantitation is performed by use of a double internal standard method. This method can separate fatty acid ethyl esters from $C_6$ to $C_{24}$.

| Equipment | |
|---|---|
| Gas Chromatograph | Hewlett-Packard 5890, or equivalent, equipped with a split injector and flame ionization detector, Hewlett-Packard Co., Scientific Instruments Div., 1601-T California Ave., Palo Alto, CA 94304 |
| Autosampler Injector | Hewlett-Packard 7673A, or equivalent |
| Column | 15 m × 0.25 mm I.D., fused silica capillary column coated with DB-WAX (0.25 micron film thickness), Hewlett-Packard Co., Scientific Instruments Div. |
| Data System | Hewlett-Packard 3350, 3000-T Hanover St., Palo Alto, CA 94304 |
| Recorder | Kipp & Zonen, BD40, Kipp & Zonen |
| Reagent | |
| Hexane | Burdick & Jackson, or equivalent, American Scientific Products |

Reference Standards

Two reference standards are used each day of operation to verify proper operation of this method. 1) A reference mixture of fatty acid methyl esters (FAME) is used to check the operation of the instrument. This reference mixture has the following fatty acid composition: 1% $C_{14:0}$, 4% $C_{16:0}$, 3% $C_{18:0}$, 45% $C_{18:1}$, 15% $C_{18:2}$, 3% $C_{18:3}$, 3% $C_{20:0}$, 3% $C_{22:0}$, 20% $C_{22:1}$, and 3% $C_{24:1}$. 2) A reference standard of a commercial shortening is used to check the operation of the total system—ethylation and gas chromatographic analysis. The shortening reference standard has the following fatty acid composition: 0.5% $C_{14:0}$, 21.4% $C_{16:0}$, 9.2% $C_{18:0}$, 40.3% $C_{18:1}$, 23.0% $C_{18:2}$, 2.2% $C_{18:3}$, 0.4% $C_{10:0}$, 1.3% $C_{20:1}$, and 0.3% $C_{22:0}$.

The reference mixture of FAME should be diluted with hexane and then injected into the instrument. A new vial of FAME reference mixture should be opened every day since the highly unsaturated components, $C_{18:2}$ and $C_{18:3}$, oxidize easily. The shortening reference standard should be ethylated with the samples prior to their analysis by capillary gas chromatography. The results from the reference standards should be compared with the known values and a judgment made concerning the completed analysis. If the results of the reference standards are equal to or within ±3 standard deviations of the known values, then the equipment, reagents and operations are performing satisfactorily.

Operation

A. Instrumental Set-up
1. Install the column in the gas chromatograph, and set up the instrumental conditions as in Table 4.
2. Set up the data system with the appropriate method to acquire and analyze the data. The retention times may have to be adjusted in the method due to instrument variations. Consult the data system reference manual on how to do this—HP3350 User's Reference Manual. Unity response factors are used for each component.
3. Obtain the shortening reference standard for analysis with the samples and ethylate it with the samples.

TABLE 4

INSTRUMENTAL CONDITIONS

| | |
|---|---|
| Instrument | Hewlett-Packard 5890 |
| Column | 15 m × 0.25 mm I.D., coated with DB-WAX, 0.25 u film thickness |
| Column head pressure | 12.5 psi |
| Carrier gas | Helium |
| Injector "A" temperature | 210° C. (410° F.) |
| Split vent flow | 100 mL/min. |
| Septum purge | 1.5 mL/min. |
| Oven temperature profile: | |
| Initial temperature | 110° C. (230° F.) |
| Initial time | 1 min. |
| Rate 1 | 15° C./min |
| Final temp 1 | 170° C. (338° F.) |
| Final time 1 | 0 min. |
| Rate 2 | 6° C./min |
| Final temp 2 | 200° C. (392° F.) |
| Final time 2 | 0 min. |
| Rate 3 | 10° C./min |
| Final temp 3 | 220° C. (428° F.) |
| Final time 3 | 8 min. |
| Detector | FID |
| Detector temp | 230° C. (446° F.) |
| Make-up gas | 30 mL/min. |
| Detector $H_2$ flow | 30 mL/min. |
| Detector air flow | 300 mL/min. |

B. Analysis of Samples— (The samples are analyzed with a double internal standard.)
1. Dilute the reference mixture of FAME with hexane. The methyl esters should be approximately 2% in hexane. Inject one microliter of this solution via the autosampler. The results must meet the criteria in the Reference Standards section.
2. Prepare the triglyceride samples to be analyzed by adding two different internal standards, $C_9$ and $C_{21}$ triglycerides. ($C_9$ and $C_{21}$ triglycerides are commercial standards consisting of 100% 9-carbon and 21-carbon triglycerides, respectively.) The internal standards are added to the samples at about 10% by weight of the sample. The samples (including the internal standards) are then converted to ethyl esters by any standard method.
3. Set up a sequence in the LAS data system to inject the samples.
4. Activate the autosampler to inject 1.0 microl. of the samples in the sequence. The gas chromatograph will automatically begin its temperature program and the data system will collect and analyze the data for the sequence.
5. The data is analyzed with the two internal standard procedure. The absolute amount (mg of esters per gram of sample) of the $C_6$ through $C_{16}$ components is calculated from the $C_9$ internal standard. The absolute amount of the $C_{18}$, $C_{20}$, $C_{22}$ and $C_{24}$ components is calculated from the $C_{21}$ internal standard. Weight percentages of fatty acids are calculated from these amounts.

4. Melting Point of Reduced Calorie Fat

| Apparatus: | |
|---|---|
| Differential Scanning Calorimeter (DSC) | Perkin-Elmer (Norwalk, CT) DSC-4 |
| Straight-side aluminum sample pans and lids | Perkin-Elmer |
| 10 ml glass vials with Teflon lined caps | |
| Balance | Analytical, micro-balance able to weigh ± 0.005 mg |
| Thermometer | |
| Hot water bath | 140° to 180° (60° C. to 82° C.) |
| 50% water/50% ice bath | |
| Constant temperature chambers at 38° F. and 70° F. (3.3° C. and 21.1° C.) | |
| Reagents | |
| Indium reference standard | Perkin-Elmer |
| Distilled water | |

The calibration of the DSC is checked before each sample is analyzed. The onset temperature of the Indium reference standard shall be compared with its known onset temperature to verify that apparatus and procedures are performing satisfactorily. If the DSC is found to be out of calibration by more than ±0.5° C., it shall be recalibrated. The DSC is recalibrated using the appropriate procedures described in the DSC Operating Manual, using the Indium and the water reference materials.

Procedure:
1. Melt sample until clear on a hot water bath, and place 2–3 grams into a 10 ml glass vial.
2. Heat sample (after adjusting hot water bath to 145° F.±2° F. [62.8° C.± 1° C.]), hold at 145° F. for 30±5 minutes.
3. Quick chill by immersing vial in water/ice bath, hold for 15±2 minutes.
4. Place vial in 38° F. (3.3° C.) chamber, hold 48±4 hours.
5. Transfer vial to 70° F. (21.1° C.) chamber, hold 48±4 hours.
6. Run the sample on a Perkin-Elmer DSC-4 as follows:

| Conditions: | |
|---|---|
| Sample weight | 5.00 mg (±0.10 mg) |

| Conditions: | |
|---|---|
| Scan rate | 2.5° C./min. for sample. |
| | 10° C./min. for refer. std. |
| Temperature range | −20 to 50° C. for sample. |
| | 150 to 165° C. for refer. std. |
| Hold time @ load temperature | 5 minutes |
| Sample pan and lid | Perkin-Elmer Straight-side |

7. Analyze the melting curve by first normalizing the thermogram. After normalizing, bracket the peak 1) at or just below the point of baseline deviation and below 10° C. and 2) at or just above the point at which the thermogram returns to the baseline and above 38° C. Draw the % solids curve.
8. Determine the % solids at 10° C., 21.1° C., 26.7° C., 33.3° C. and 37.8° C.
9. Record the complete melt point as the temperature at which the % solids curve returns to the baseline.

5. Rate of Crystallization into Beta Phase

This method is used to calculate the rate of crystallization of a reduced calorie fat sample into beta form. X-ray diffraction techniques are commonly used to characterize crystalline polymorphs in triglycerides. When fat crystals are analyzed by x-ray, two types of spacing data can be collected. Long spacing data is observed in the 2θ range from 1°–15° (89 to 5.9 Å) and short spacing data in the 2θ range from 16°–27° (5.5 to 3.3Å). The long spacing data correspond to the planes formed by the methyl end groups of the triglycerides and are dependent on chain length and angle of tilt of the molecule. Short spacings refer to the cross-sectional packing of the hydrocarbon chains. Short spacings are commonly used to characterize the polymorphic forms of fats.

X-ray diffraction analyses are made with a Philips XRG3 100 unit (Philips Electronic Instruments, Mahwah, N.J.). It is operated at 40 kV/35 mA with monochromatic copper $K\alpha_1$ radiation as the x-ray source. This unit is interfaced with a Theta. XRD automation system form Dapple Systems, Sunnyvale, Calif., that provides stepping motor control of the two theta angle and a data processing microcomputer system.

Reduced calorie fat samples are melted and held at 140° F. (60° C.) for one hour to remove any traces of crystal memory. Empty 1.5×1.5 inch stainless steel sample holders are equilibrated at the initial tempering temperature for the reduced calorie fat samples (usually 42° F.) in the constant temperature room. The melted reduced calorie fat samples are pipetted into the sample holders. The samples are retained in the sample holders by a Scotch tape backing. A 22×22 mm microscope coverglass can be placed on the back of the holder between the tape and the sample if the sample is particularly soft. This technique can also be used to protect samples from tape contamination when samples in limited supply need to be retained after x-ray analysis.

The samples are then quickly cooled to 42° F. by transferring the samples to a 42° F. constant temperature room. The surface of the sample is smoothed/leveled so that it is even with the face of the sample holder. It is convenient to use the edge of a glass microscope slide to level the surface. The sample is held at 42° F. for one hour, and then moved to a 70° F. constant temperature room.

The samples are monitored for beta growth. X-ray diffraction data is collected at regular time intervals. (To minimize the amount of temperature change in the tempered samples, they are transported in an insulated box from the temperature storage to the x-ray unit). The amount of beta was determined from peak area at 4.54 angstroms. Short spacing data is quickly collected by scanning from 17° to 25° 2θ at 0.05 step increments with 1 second hold times. For long spacing data, samples are scanned from 1.45 to 30° 2θ with 0.025 step increments and 1 second hold times.

EXAMPLES

The following are specific examples to illustrate the making of MML/MLM triglycerides which are enriched in long chain fatty acid 2-position isomers according to the process of the present invention:

EXAMPLE 1

$C_{10:0}$ (P&G C1095) fatty acid is redistilled to improve color, odor and reduce unsaponifiable levels. The $C_{10:0}$ acid is distilled at 170°190° C. under vacuum and condensed at 40° C. An 80% middle-cut fraction of the distillate yielded a 97.5% pure $C_{10:0}$ fatty acid feedstock. $C_{8:0}$ (P&G C895) fatty acid of 97.7% purity is also used.

A selective esterification reaction is made in a pilot plant reaction system. The reactor consists of a hot oil heated 200 liter vessel having a variable speed agitator (3.14 cm diameter), no internal baffles, and a gas dispersion ring connected to an external nitrogen source directly below the agitator. A partial condenser consisting of a reflux column (1.96 cm diameter.times. 22.04 cm length) packed with metal wire mesh and a horizontal condenser are connected to the top of the reactor vessel. Total condenser capability is provided by a separate condenser / distillate trap.

Typically, about 118 kg of a mixture of $C_{10:0}$ and $C_{8:0}$ fatty acids (55:45 weight ratio) is preheated to the esterification temperature and adjusted to the requisite pressure. This fatty acid mixture is used to esterify about 16.8 kg of monobehenin at an 18:1 acid to monobehenin mole ratio at esterification temperature 245° C. (The monobehenin is commercially produced by molecular distillation of behenic acid/glycerol reaction products and comprises 98.1% monoglyceride, 0.5% diglyceride, 0.1% free glycerol, and 0.3% diglycerol.) The monobehenin is added incrementally as a liquid over a 60 minute period to the melted fatty acids. The esterification pressure ranges from 700 mmHg to 1520 mmHg. A pressure of 700 mmHg is initially used, but is increased as necessary to prevent the mixture containing the fatty acids from boiling over.

Vigorous agitation (571 m/min. tip speed) and a nitrogen gas sparging rate of 1.4–2.1 liter/min. per liter of reaction mixture is used to remove the water generated during the esterification. The light fatty acids are refluxed by the partial condenser operated at 110° C., while generated water is condensed by the total condenser at 40° C. The esterification progress is monitored by thin layer chromatography (TLC) using high performance silica plates and a 75 part petroleum ether/25 part diethyl ether/1 part acetic acid development solvent, followed by charring with 5% phosphomolybdic acid in anhydrous methanol. The esterifications are stopped after complete elimination of diglycerides (i.e. measured level typically less than 0.4%).

Analyses of the reaction mixture after the esterification reaction indicates a 6% MMM, 91.3% MML/MLM and 2.7% MLL/LML triglyceride composition (average) in the reaction mixture. (As determined by CNP (acid free basis), "MMM" $C_{24}$ to $C_{34}$, "MML/MLM"=$C_{36}$ to $C_{44}$, and "MLL/LML" $C_{46}$ to $C_{56}$.)

Residual fatty acids are vacuum distilled from the reaction mixture in a Pfaudler wiped-film distillation unit. Typical residual fatty acid levels are 78% (as oleic) at the start of the distillation. The stripping temperatures range from 169°–202° C. with vacuum levels of 2 to 50 mm Hg. Distillation is stopped when the residual fatty acids are reduced to less than about 5%. The stripped batch is cooled to 100° C. by an external heat exchanger. Analysis of the stripped batch indicates a 6.0% MMM, 91.3% MML/MLM and 2.7% MLL/LML triglycedde composition (average), which suggests excellent thermal stability for the reaction mixture. The fatty acid composition of the stripped batch is as follows: 1% C6:0, 48% combined $C_{8:0}$ and $C_{10:0}$, <1% $C_{12:0}$, <1% $C_{14:0}$, 0.7% $C_{16:0}$, 0.8% $C_{20:0}$, 48% $C_{22:0}$, and <1% $C_{24:0}$ fatty acids (average).

The stripped batch is decolorized by addition of 3% Filtrol® 105 bleaching earth/0.3% Norit® 2203 activated carbon. The slurry of bleaching agents and stripped oil is heated at 75° C. for 3 hours prior to the addition of diatomaceous filter earth. The mixture is filtered through a plate and frame filter press, and yields a clear oil. Analysis of the bleached product indicates a 6.0% MMM, 91.3% MML/MLM and 2.7% MLL/LML triglyceride composition (average), and 5% free fatty acids (as oleic).

The residual fatty acids and MMM triglycerides are removed by molecular distillation on a KD-10 unit (UIC, Inc.). The stripped batches are fed to the unit at a 6 kg./hr. feed rate and a portion thereof is distilled at 8 microns pressure and a 200° C. wall jacket temperature. Under these conditions, a 15% distillate cut is made which removes all residual fatty acids and most MMM triglycerides. Composite analysis of the molecular still residue indicated a 2.0% MMM, 95.0% MML/MLM and 3.0% MLL/LML tdglycerides composition (average). The level of unsaponifiables is 1% in the reaction mixture. A second cut is done to reduce the level of MMM triglycerides to less than 1%.

The residue from the distillation is passed through a KD-10 molecular still to separate the desired MML/MLM triglycerides from the MLL/LML triglycerides and residual color/unsaponifiables. A feed rate of 6 kg./hr. and a 250° C. wall jacket temperature at 4 microns pressure is used to distill off the desired MML/MLM triglycerides. An 85% cut is taken.

Analyses of the distillate indicates a 1.5% MMM, 43.1% MML, 54.8% MLM (97.9% combined MML and MLM triglycerides) and 0.6% MML/LML triglyceride composition (average). The level of unsaponifiables is 0.25% in the distilled product which suggests good separation of these components by molecular distillation. The melting point of the triglyceride mixture is 29.1° C. 56% of the triglycerides having a carbon number of 42 are MLM triglycerides.

The distilled MML/MLM triglycerides are then deodorized at 205° C. for 3 hours at a pressure of 1–2 mmHg with a 1.0% steam rate. The distilled, bleached and deodorized MML/MLM triglycerides are clear in color, odor-free and bland in taste. Follow-up evaluations in chocolate-flavored products indicate good utility as a cocoa butter replacer. This blend crystallizes into beta form within about 1 hour. Overall yield of purified MML/MLM triglycerides is 65% based on the initial amount of monobehenin.

EXAMPLE 2

$C_{8:0}$ (P&G C895) and $C_{10:0}$ (P&G C1095) fatty acids having 95% purity are redistilled to remove color, odor and reduce unsaponifiable levels. Approximately 1000 grams of the respective acid is placed in a 3 liter three-necked round bottom flask. Heat is applied by a thermostatically controlled heating mantle. The acids are condensed by a cold trap into a receiving flask. About 80% of the respective acid is distilled, yielding 98.6% pure $C_{8:0}$ and 97.1% pure $C_{10:0}$ fatty acid feedstocks.

One hundred twenty (120) grams of monobehenin (commercially produced by molecular distillation of a behenic acid/glycerol reaction product feed) is esterified using an 18:1 acid to monobehenin mole ratio at a temperature of 225° C. for 180 minutes and a pressure of 500 ramrig. The fatty acids are added on an equal mole basis (55% $C_{10:0}$/0/45% $C_{8:0}$). The monobehenin contains 95.8% monoglyceride, 2.6% diglyceride, and 0.36% glycerol. Progress of the esterification is monitored by TLC using the procedure described in Example 1.

Excess fatty acids are vacuum distilled from the reaction vessel using a cold water condenser and collection trap. The initial free fatty acid level of the completed esterification is 78% (as oleic fatty acid). Over a four hour period, free fatty acid is reduced to 2% by heating the reaction mixture at 115°150° C. using a 0.25–1 mm Hg vacuum.

The overall synthesis yield of the MML/MLM triglycerides is 92.7% (calculated on the basis of the starting monobehenin purity). Key compositional data were as follows:

|  | After Esterification | After Acid Removal |
|---|---|---|
| Fatty Acid (% as $C_{10:0}$) | 78 | 2.0 |
| Glyceride Composition* |  |  |
| MMM (%) | 4.6 | 3.8 |
| MLM (%) | 43.5 | 43.9 |
| MML (%) | 49.1 | 49.5 |
| combined MML/MLM (%) | 92.6 | 93.4 |
| MLL/LML (%) | 2.8 | 2.8 |
| ML(OH) (%) | 0.25 | 0.3 |
| Fatty Acid Profile |  |  |
| $C_{8:0}$ | 23.4 | 23.4 |
| $C_{10:0}$ | 27 | 27 |
| $C_{12:0}$ | 0.4 | 0.4 |
| $C_{14:0}$ | — | — |
| $C_{20:0}$ | — | — |
| $C_{22:0}$ | 49 | 49 |
| $C_{24:0}$ | 0.2 | 0.2 |

*By CNP (acid free basis): "MMM" = $C_{24}$ to $C_{34}$, "ML(OH)" = $C_{30}$ to $C_{32}$, "MML/MLM" = $C_{36}$ to $C_{44}$, "MLL/LML" = $C_{46}$ to $C_{56}$ The acid stripped mixture is distilled and deodorized as described hereinbefore in Example 1. Carbon number profiles (CNP) indicate a 1% MMM, 46.0% MLM, 51.8% MML (97.8% combined MML/MLM) and 1.2% MLL/LML triglyceride composition. the melting point of this composition is 29.1° C. 47% of the triglycerides having a carbon number of 42 are MLM triglycerides. Overall yield of purified MML/MLM triglycerides is 70% based on the starting amount of monobehenin.

The level of MLM triglycerides can be increased to 75% by crystallizing the composition in acetone. The composition is dissolved in acetone at about a 4:1 ratio of acetone to reduced calorie fat and heated to complete dissolution (about 50° C.). The solution is cooled to about 0° C. and fractions taken over time. The first fraction contains high levels of MMM & MML triglycerides. The second fraction contains some MML, primarily MLM, and some MLL/LML. The third fraction contains primarily MLL/LML.

EXAMPLE 3

The process described in this example can be divided into four major steps:

(A) esterification of glycerol with C8/C10 fatty acids to form a mixture of mono-, di-, and tri-medium chain glycerides;

(B) recovery of the MM-diglyceride fraction;

(C) esterification of the MM-diglycerides with behenic arthydride at relatively low temperature via use of a catalyst; and (D) recovery of the mono-long fraction.

Initially, glycerol is esterified with C8 and C 10 fatty acids to form a mixture of mono-, di, and tri, C8/C10 glycerides. The reaction uses an equimolar mix of C8/C 10 fatty acid and glycerol at a 1.3:1.0 molar ratio. Total batch weight is about 280 pounds. The reactor is sparged with N2 at about 1.0 liter per liter of mixture per hour. After charging the reactor with both the fatty acids and glycerol, the reaction mix is heated to 225° C. and held for 30 minutes to ensure that equilibrium is reached. Thin-layer chromatography is used to monitor the reaction. This mixture is vacuum distilled in the batch reactor to remove as much glycerine and excess fatty acid as possible prior to introduction into the KD-10 molecular distillation unit.

The mixture is fed to the KD-10 unit at about 12 pounds per hour with a vacuum level of 20 microns and a temperature of about 160° C. to remove any remaining glycerine and fatty acids, along with a portion of the monoglyceride fraction. A cut of 20% is taken. A second cut of 15% is taken at 180° C. to remove the remaining portion of monoglycerides to less than 2%. Next, a recovery step is carried out with the second cut distillate in order to recover a large amount of MM-diglyceride. This recovery step is run at 175° C. and 10 microns with a flow rate of 15 pounds per hour to obtain a 50% cut with the residue fraction retained as the MM-diglyceride portion. A low level of M-monoglycerides is important in order to minimize the formation of undesirable MLL's during the next reaction step.

The remaining di-, triglyceride mixture is distilled in two cuts to collect the diglyceride fraction and keep the amount of MMM's to less than about 10%. This reaction is run at about 180° C. and 15 microns at a flow rate of about 12 pounds per hour. The diglyceride mid-fraction contains about 3.5% monoglycerides, about 84.8% diglycerides, and about 11.7% triglycerides. About 95 pounds of the mid-fraction is recovered.

Next, the MM-diglyceride fraction is esterified with behenic anhydride over a zinc chloride catalyst (0.035 wt %) at about 80° C. A 1.1:1.0 molar ratio of behenic anhydride to MM-diglycerides is used. Total weight of the batch is about 290 pounds. After the reactor is charged with the behenic anhydride, the MM-diglyceride fraction is metered into the vessel over a one hour period. The reaction mix was monitored via TLC to ensure near complete conversion to triglyceride (<0.4% diglycefide). The use of behenic anhydride for the acylation, along with a catalyst, allows the reaction to be run at a low enough temperature to maintain position specificity. That is, the product from this reaction will be 40% MML and 60% MLM as based on the ratio of 1,2- and 1,3-diglycerides formed from the first reaction.

Next, a water washing step is carried out to remove the catalyst. In this step, NaCl is used to break the water-in-oil emulsion. The water washing step is carried out in the batch reactor at about 80° C. and atmospheric pressure of N2. A small amount of C8/C10 medium chain fatty acid anhydride (1.1% wt) is added to the reaction mixture and contacted for about one hour at about 60° C. to reduce the level of ML-diglycerides. About 100 pounds of distilled water is added and allowed to settle for several hours. The mixture is decanted and a 50 pound charge of 10% salt water is added. After allowing the system to settle, the remaining water is decanted. Afterwards, the reactor is evacuated to remove any trace amounts of water and the product is filtered through a cartridge filter.

After the above steps, the material is passed through the KD-10 unit to distill over initially the MMM and the MML/MLM fractions. This is done in order to separate the bottoms from the mixture first. This allows the bottoms fraction (MLL's, soap, residues, etc.) to pass through the KD-10 unit only once. The unit is run at about 275° C. with a flow rate of 15 pounds per hour and a pressure of about 16 microns.

At this point, the mixture contains about 40% behenic acid. Three passes are required to lower the $C_{22}$ fatty acid level in the mix from 40% down to about 0.6%. The cuts are taken at 220° C. and 12 microns and 12, 10, and 8 pounds per hour flow rate, respectively. The cuts are 30%, 25% and 15%, respectively. The last cut also took off about 50% of the MMM's. A fourth cut run at 10 pounds per hour and about 250° C. is required to get the MMM level to about 1.5%. At this point, the 2-position level is measured and found to be 60% for each of the CN38, CN40, and CN42 carbon numbers.

The mixture was then deodorized in the batch reactor at 400oF for three hours and 1.0% steam rate. About 88 pounds of 60% long chain fatty acid 2-position isomer is recovered.

What is claimed is:

1. A reduced calorie fat which comprises MLM/MML triglycerides and which is enriched in MLM triglycerides, wherein M is a $C_6$ to $C_{10}$ fatty acid residue or mixture thereof and L is a $C_{17}$ to $C_{26}$ fatty acid residue or mixture thereof, wherein said reduced calorie fat comprises:

(a) at least about 40% MLM triglycerides;

(b) at least about 85% combined MML and MLM triglycerides;

(c) no more than about 5% combined LLM and LML triglycerides;

(d) no more than about 2% LLL triglycerides;

(e) no more than about 4% MMM triglycerides; and (f) no more than about 6% other triglycerides; and wherein the reduced calorie fat has the following fatty acid composition by weight percent:

(a) from about 15 to about 70% $C_6$ to $C_{10}$ saturated fatty acids;

(b) from about 10 to about 70% $C_{17}$ to $C_{26}$ saturated fatty acids;

(c) no more than about 10% fatty acids selected from the group consisting of $C_{12:0}$ and $C_{14:0}$ and mixtures thereof, (d) no more than about 20% fatty acids selected from the group consisting of $C_{18:1}$, $C_{18:2}$, $C_{18:3}$ and mixtures thereof; and (e) not more than about 4% $C_{18:2}$ fatty acids.

2. The reduced calorie fat of claim 1 which crystallizes into the stable beta form in less than about 8 hours.

3. The reduced calorie fat of claim 2 which has a complete melting point ranging from about 28° C. to about 60° C.

4. The reduced calorie fat of claim 3 wherein the fat comprises at least about 45% MLM triglycerides.

5. The reduced calorie fat of claim 4 wherein the fat comprises at least about 90% by weight MLM/MML triglycerides.

6. The reduced calorie fat of claim 5 wherein the fat comprises no more than about 3% combined LLM/LML triglycerides.

7. The reduced calorie fat of claim 6 wherein the mole ratio of C8 to C10 saturated fatty acid present in the fat ranges from about 30:70 to about 70:30.

8. The reduced calorie fat of claim 7 wherein the fat comprises at least about 60% MLM triglycerides.

9. The reduced calorie fat of claim 8 wherein the fat comprises at least about 94% combined MLM/MML triglycerides.

10. The reduced calorie fat of claim 9 wherein from about 40 to about 100% of the triglycerides have a carbon number of 42.

11. The reduced calorie fat of claim 10 wherein the fat crystallizes into the stable beta phase form in less than about 4 hours.

12. The reduced calorie fat of claim 11 wherein the fat comprises no more than about 1% combined LLM and LML triglycerides.

13. The reduced calorie fat of claim 12 wherein from about 45% to 100% of the triglycerides having a carbon number of 42 are MLM triglycerides.

14. The reduced calorie fat of claim 13 wherein the fat crystallizes into the stable beta phase in less than about 2 hours.

15. The reduced calorie fat of claim 14 wherein the fat crystallizes into the stable beta phase in less than about 1 hour.

16. The reduced calorie fat of claim 15 wherein the fat crystallizes into the stable beta phase in less than 30 minutes.

17. The reduced calorie fat of claim 16 which has melting point ranging from 31° C. to 45° C.

18. A reduced calorie fat which comprises MLM/MML triglyceride isomers and which is enriched in MLM triglyceride isomers, wherein M is a $C_6$ to $C_{10}$ fatty acid residue or mixture thereof and L is a $C_{17}$ to $C_{26}$ fatty acid residue or mixture thereof, wherein said reduced caloric fat comprises:

(a) more than 40% of said MLM triglyceride isomers;

(b) at least about 85% of said MML and MLM triglyceride isomers;

(c) no more than about 5% combined LLM and LML triglycerides;

(d) no more than about 2% LLL triglycerides;

(e) no more than about 4% MMM triglycerides; and (f) no more than about 6% other triglycerides; and wherein the reduced calorie fat has the following fatty acid composition by weight percent:

(a) from about 15 to about 70% $C_6$ to $C_{10}$ saturated fatty acids;

(b) from about 10 to about 70% $C_{17}$ to $C_{26}$ saturated fatty acids;

(c) no more than about 10% fatty acids selected from the group consisting of $C_{12:0}$ and $C_{14:0}$ and mixtures thereof;

(d) no more than about 20% fatty acids selected from the group consisting of $C_{18:1}$, $C_{18:2}$, $C_{18:3}$ and mixtures thereof; and (e) not more than 4% $C_{18:2}$ fatty acids.

\* \* \* \* \*